(12) United States Patent
Donitzky et al.

(10) Patent No.: US 9,033,506 B2
(45) Date of Patent: May 19, 2015

(54) APPARATUS AND METHOD FOR OPTICAL COHERENCE TOMOGRAPHY

(75) Inventors: Christof Donitzky, Eckental/Eschenau (DE); Klaus Vogler, Eckental/Eschenau (DE); Christian Wuellner, Moehrendorf (DE); Claudia Gorschboth, Nuremberg (DE); Michael Mrochen, Eglisau (CH)

(73) Assignee: Wavelight GMBH (DE)

( * ) Notice: Subject to any disclaimer, the term of this patent is extended or adjusted under 35 U.S.C. 154(b) by 0 days.

(21) Appl. No.: 13/984,574

(22) PCT Filed: Feb. 15, 2011

(86) PCT No.: PCT/EP2011/000712
§ 371 (c)(1),
(2), (4) Date: Sep. 5, 2013

(87) PCT Pub. No.: WO2012/110052
PCT Pub. Date: Aug. 23, 2012

(65) Prior Publication Data
US 2014/0009743 A1  Jan. 9, 2014

(51) Int. Cl.
*A61B 3/10* (2006.01)
*A61B 3/00* (2006.01)
(Continued)

(52) U.S. Cl.
CPC ............... *A61B 3/102* (2013.01); *A61B 3/1225* (2013.01); *A61B 5/0066* (2013.01)

(58) Field of Classification Search
CPC ........ A61B 13/14; A61B 3/103; A61B 3/113; A61B 3/1225; A61B 3/1015
USPC .................. 351/206, 221, 200, 205, 210, 246
See application file for complete search history.

(56) References Cited

U.S. PATENT DOCUMENTS

2008/0208018 A1* 8/2008 Ridder et al. ................. 600/322
2008/0231807 A1  9/2008 Lacombe et al.
(Continued)

FOREIGN PATENT DOCUMENTS

EP       0697611 A2   2/1996
JP       2007521866   8/2007
(Continued)

OTHER PUBLICATIONS

Watanabe, "Three-dimensional imaging by ultrahigh-speed axial-lateral parallel time domain optical coherence tomography", Jun. 12, 2006, Optics Express, vol. 14, No. 12, pp. 1-9.*
(Continued)

*Primary Examiner* — Dawayne A Pinkney (57) ABSTRACT

There is provided an apparatus for recording a depth profile of a biological tissue, in particular a frontal eye section of a human eye, according to the principle of optical coherence tomography, comprising a light source adapted to generate a bundle of light rays, an interferometer arrangement having a beam splitter device adapted to spatially separate the bundle of light rays into a reference beam and a measurement beam directed toward the tissue, a reference beam deflection device adapted to deflect the reference beam, a beam superpositioning device adapted to spatially superimpose the deflected reference beam onto the measurement beam deflected by the tissue into a superpositioned beam, and a detector arrangement for detecting information in the superpositioned beam associated with the difference of the optical path length of the reference beam and the measurement beam.

19 Claims, 4 Drawing Sheets

(51) Int. Cl.
*A61B 3/14* (2006.01)
*A61B 3/12* (2006.01)
*A61B 5/00* (2006.01)

(56) References Cited

U.S. PATENT DOCUMENTS

| | | |
|---|---|---|
| 2009/0185191 A1 | 7/2009 | Boppart et al. |
| 2010/0103374 A1* | 4/2010 | Hirose et al. ............ 351/206 |
| 2010/0166293 A1 | 7/2010 | Sugita et al. |
| 2010/0182567 A1* | 7/2010 | Nouchi et al. ........... 351/208 |
| 2011/0102740 A1* | 5/2011 | Hirose .................... 351/206 |
| 2011/0242487 A1* | 10/2011 | Yuasa et al. ............. 351/206 |
| 2013/0078733 A1* | 3/2013 | Holmes et al. .......... 436/174 |

FOREIGN PATENT DOCUMENTS

| | | |
|---|---|---|
| WO | 2009011088 | 1/2009 |
| WO | 2010150483 A2 | 12/2010 |
| WO | 2012110052 A1 | 8/2012 |

OTHER PUBLICATIONS

International Search Report and Written Opinion dated Oct. 24, 2011; corresponding to PCT Application Serial No. PCT/EP2011/000712.

Kawana et al; Anterior Segment Optical Coherence Tomography: Device Overview; New Optical Coherence Tomography (OCT) Buyer;s Guide; 25(5): 623629, 2008.

\* cited by examiner

APPARATUS AND METHOD FOR OPTICAL COHERENCE TOMOGRAPHY

TECHNICAL FIELD

The present invention relates to an apparatus and a method for recording resp. measuring a depth profile of a sufficiently transparent object to be investigated, in particular a frontal eye section of a human eye, according to the principle of optical coherence tomography.

BACKGROUND

The optical coherence tomography (OCT) is an interferometric investigation method, wherein light having a relatively low coherence length is used to measure the distances resp. depth profiles of reflecting (at least partially reflecting) materials with the aid of an interferometer arrangement. Advantages of the optical coherence tomography over competing methods are the relatively great penetration depth (approximately 1 to 3 mm) in a scattering biological tissue and at the same time the relatively high axial resolution (approximately 1 to 15 μm) at a high measurement frequency (currently, approximately 20 to 300 kVoxel/s are achieved).

SUMMARY OF EXAMPLE EMBODIMENTS

In relation to the aforementioned measurement objective, the ultrasound diagnostics (sonography) is an acoustic method corresponding to the OCT. The OCT differs from the angular dependent 3D-measurement methods (as also used by the human vision apparatus comprising two eyes) by its pure determination of the axial depth using a spectral range of the used wavelength (instead of an angular range) and its independency from the numerical aperture of the measurement apparatus associated therewith.

In the currently used OCT-measurement apparatuses, there is used light comprising wavelengths greater than 800 nm and in the ophthalmology in the range from 800 to 1300 nm. In order to measure depth profiles in the retina, light having a wavelength of approximately 840 nm is preferably used. A further wavelength that is used is next to 1060 nm.

The following equation (1) allows to calculate the axial resolution $\Delta z$, which is achieved by an OCT apparatus for a wavelength spectrum centered around a central wavelength $\lambda_0$ and having a Gaussian distribution of the bandwidth $\Delta \lambda$ (full width at half maximum, FWHM):

$$\Delta z = \frac{2 \cdot \ln(2) \cdot (\lambda_0)^2}{\pi \cdot \Delta \lambda}. \quad (1)$$

In equation (1), the constant pre-factors depend on the shape resp. form of the wavelength spectrum. The fundamental dependency of the axial resolution $\Delta z$ from the wavelength spectrum is given in that $\Delta z$ is proportional to the ratio of the square of the operating resp. central wavelength $\lambda_0$ divided by the spectral bandwidth $\Delta \lambda$, i.e. $\Delta z \propto (\lambda_0)^2/\Delta \lambda$.

Figure 1:
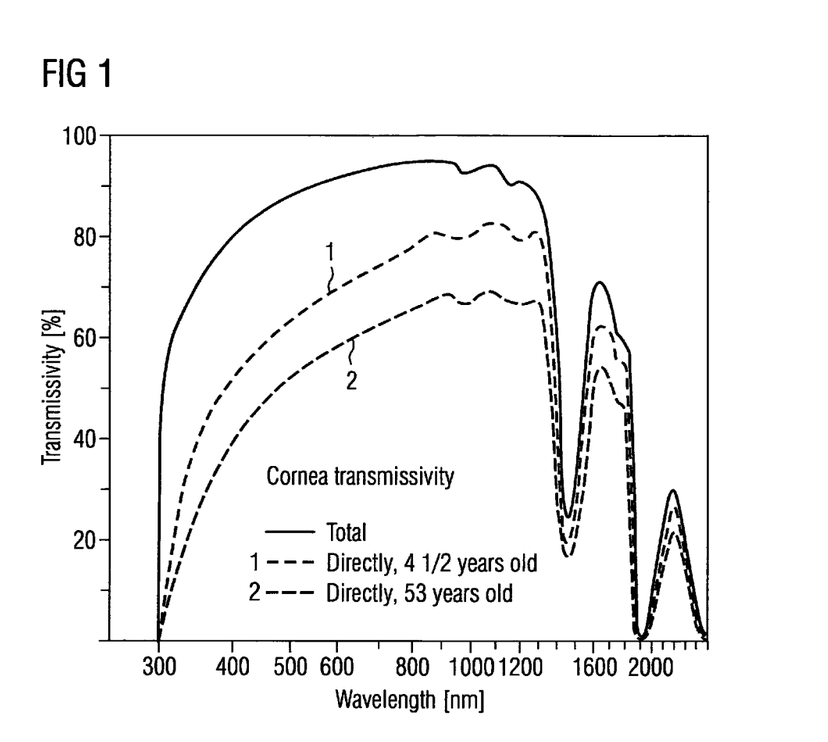
FIG. 1 shows a degree of transmission of a cornea of a human eye.

FIG. 1 shows the degree of transmission of a frontal eye section, in particular the cornea of a human eye in dependency from the wavelength, in particular for an eye at the age of 4½ years and an eye at the age of 53 years. As can be seen in FIG. 1, the degree of transmission is particularly high in a wavelength range from about 800 nm to about 1300 nm and then decreases strongly at greater wavelengths, which decrease is caused by the onset of absorption of water molecules (absorption band of the OH-stretching vibration). Due to the particularly high degree of transmission in the aforementioned wavelength range, there is achieved a high penetration depth. This is a main reason for the use of wavelengths greater than 800 nm in present day OCT-measurement apparatuses in the ophthalmology.

Figure 2:
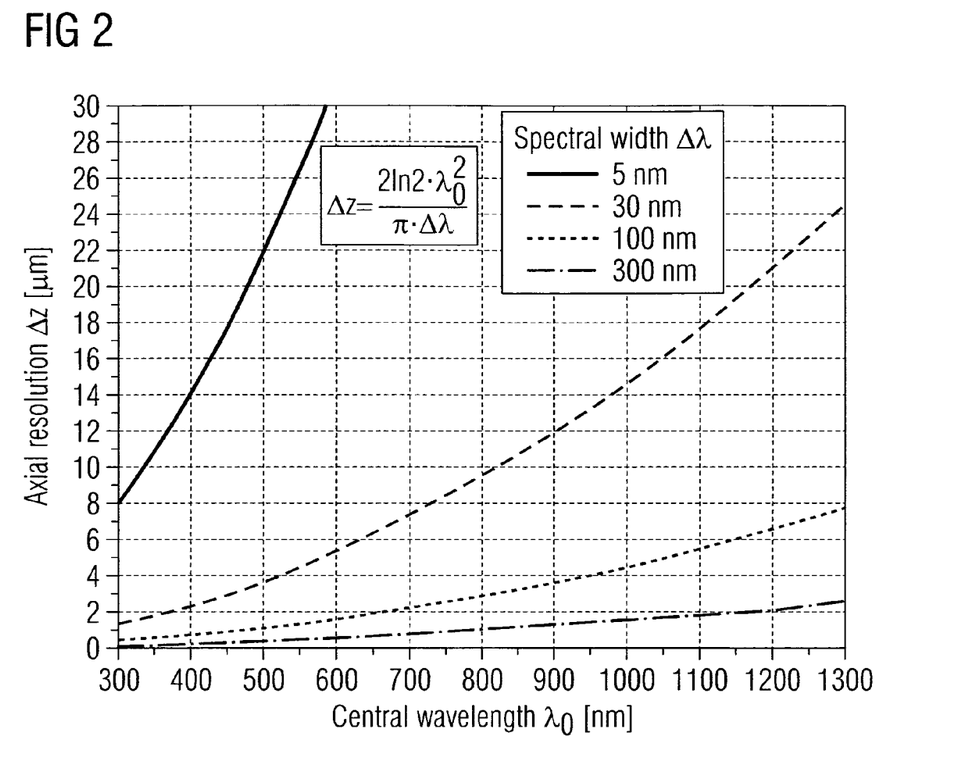
FIG. 2 shows the axial resolution $\Delta z$ of an OCT-measurement apparatus as a function of a central wavelength $\lambda_0$ for different spectral widths $\Delta \lambda$ of the used radiation.

It is a disadvantage of the OCT-measurement apparatuses, which are presently used in the ophthalmology, and which use the long-wave radiation of more than 800 nm, that the bandwidth required for achieving a sufficient axial resolution of approximately 10 μm or less can only be achieved by complex, i.e. costly broad-band light sources. In the ophthalmology, an axial resolution of 10 μm or less is required in order to be able to resolve and distinguish intra-corneal layers or to be able to define cutting surfaces sufficiently precisely. FIG. 2 serves to demonstrate the relationship prescribed by the equation (1).

FIG. 2 shows the axial resolution $\Delta z$ of an OCT-measurement apparatus as a function of the central wavelength $\lambda_0$ for radiation having different spectral bandwidths $\Delta \lambda$. In FIG. 2, curves are shown for radiation having bandwidths $\Delta \lambda$ of 5 nm, 30 nm, 100 nm and 300 nm.

In order to achieve e.g. an axial resolution of approximately 10 μm with a central wavelength of 800 nm, a spectral width of almost 30 nm is required. In order to achieve a $\Delta z$ of approximately 5 μm, a spectral width $\Delta \lambda$ of about 60 nm is required for radiation having $\lambda_0$=800 nm and a spectral width $\Delta \lambda$ of approximately 100 nm is required for radiation having $\lambda_0$=1100 nm.

It is an object of the present invention to provide an OCT-measurement apparatus, which enables obtaining a high axial resolution with little complexity.

The object is achieved by an apparatus according to claim 1 and a method according to claim 12.

Accordingly, there is provided an apparatus for recording a depth profile of a biological tissue, in particular a frontal eye section of a human eye, according to the principle of the optical coherence tomography. The apparatus comprises: a light source adapted to generate a bundle of light rays comprising wavelengths in a predetermined wavelength range and comprising an operating wavelength, an interferometer arrangement comprising a beam splitter device adapted to spatially separate the bundle of rays generated by the light source into a reference beam and a measurement beam directed toward the biological tissue, a reference beam deflection device adapted to deflect the reference beam, a beam superposition device adapted to spatially superimpose the deflected reference beam onto a measurement beam deflected by the biological tissue to a superpositioned beam, and a detector arrangement for detecting information in the superpositioned beam associated with the difference of the optical path lengths of the reference beam and the measurement beam.

According to the invention, the predetermined wavelength range is a range from more than 300 nm to 500 nm.

The use of wavelength in the range from more than 300 nm to 500 nm enables, in comparison to the wavelength used in conventional OCT-measurement apparatuses, in order to achieve a greater axial resolution at a same bandwidth, respectively to use a light source having a considerably lower bandwidth in order to achieve a comparable axial resolution.

The invention is based on the finding, that in particular in the cornea of the human eye, the scattering properties of the tissue enables obtaining a high signal intensity for the used wavelengths at a relatively low intensity of the incident light. In the present invention, it is preferable to use superluminescent diodes as the light source. Thus it is possible to obtain a compact overall configuration of the measurement apparatus at the same time with a use of reasonably priced, stable and reliable light sources.

Preferably, the predetermined wavelength range is a range from 350 nm to 450 nm, more preferably from 395 nm to 415 nm and particularly preferred next to 405 nm. Semi-conductor laser diodes, in particular gallium nitride (GaNi)-semiconductor LEDs, are preferably used as the light source in these wavelength ranges.

Preferably, the interferometer arrangement and the detector arrangement are designed for an operation using wavelengths in the aforementioned wavelength range. For example, a reflecting layer of the reference beam deflection device is formed such that its reflectivity is particularly high for the used wavelengths within the aforementioned range. Accordingly, also the beam splitter device and/or the beam superpositioning device can be formed accordingly such that their degree of transmission is particularly high for the used wavelengths. Finally, also the detector arrangement can be designed such that its sensitivity for detecting light (sensitivity) is particularly high for the used wavelengths.

The apparatus can be designed such that it operates according to the principle of the Fourier-domain-OCT. To this end, the reference beam may run spatially substantially constant and the detector arrangement may comprise a spectrometer device, in particular a prism or an optical grating, which separates the superpositioned beam spatially, according to the wavelength, into partial beams having different wavelengths, and a spatially resolving detector array, which measures the intensity of the partial rays in a wavelength selective manner. The thus designed apparatus comprises no moving optical elements resp. moving elements which influence the beam direction, and thus enables a temporally stable measurement sensitivity.

Alternatively, the apparatus can be designed such that it operates according to the principle of the time-domain-OCT. To this end, the optical path length of the reference beam can be modulated temporally, in particular by a periodic movement of the reference beam deflection device, and the detector arrangement may comprise a detector device which measures the intensity of the superpositioned beam which is temporally modulated by the modulation of the reference beam. Thus, the sampling rate of the detector is greater than the modulation frequency of the reference beam, preferably two-times and in particular ten-times as high. A thus constructed apparatus can be designed to have a more simply constructed detector, which receives a spatially limited bundle of rays, i.e. the detector arrangement does not require a spectrometer device as in the case of a Fourier-domain-OCT device.

Particularly preferred is an apparatus, which operates according to the principle of the parallel time-domain-OCT. Such an apparatus comprises a light source comprising a related collimator optic, which generates a widened parallel beam of light, wherein the width of the beam of light is for example in the range from 2 to 10 mm, preferably from 4 to 8 mm and more preferably from 5 to 7 mm. In particular, the beam width can be selected so that the total area of the biological tissue to be investigated (for example the total area of the cornea or the callus of the human eye) is eradiated with parallel light. A detector arrangement suitable for use in a parallel time-domain-OCT apparatus comprises an imaging optics and a two-dimensional detector array, wherein the imaging optics is arranged in the optical path between the beam superpositioning device and the detector array, such that it images (focuses) the parallel light from the beam superpositioning device into a detection plane arranged perpendicular to an optical axis of the detector arrangement. It is an advantage of such a construction, that a relatively large, in particular the total, area of the biological tissue to be investigated is captured simultaneously. This enables a shorter measurement time and enables that it is no longer required to scan the measurement beam across the surface resp. area of the tissue to be investigated (i.e. to deflect it in a direction perpendicular to an optical axis of the measurement beam).

Depending on the construction of the light generating element of the light source, the light source may also comprise an imaging optics which generates a bundle of light rays having a suitable beam shape, for example a focussed beam or a beam of parallel light. Accordingly, the detector arrangement may comprise an imaging element which images (focuses) the parallel, widened superpositioned beam onto a light detector.

The apparatus may comprise, for a coherent imaging of the tissue onto the detector, in the measurement beam a measurement optical system and in the superposition beam a first superposition beam optical system.

The apparatus may further comprise in the reference beam a reference beam optical system for a correction of phase differences between the reference beam and the measurement beam caused by optical wavelength portions of the measurement beam within the tissue.

The apparatus may further comprise in the superpositioned beam a second superposition beam optical system for a correction of imaging errors caused by a predetermined basic shape respectively form, such as a basic arching of the biological tissue such as the frontal eye section, provided in the measurement beam.

The apparatus described above can be suitable to measure and visualize infra-corneal layers of a human eye. The apparatus may have an axial resolution of 10 µm, preferably of 5 µm and more preferably of 2 µm.

In a method for measuring a depth profile of a biological tissue, in particular a frontal eye section of a human eye, according to the principle of optical coherence tomography, there is used light comprising wavelengths in a predetermined wavelength range having a predetermined bandwidth and comprising an operating wavelength.

According to the invention, also herein, the predetermined wavelength range is a range of more than 300 nm to 500 nm.

In the method, it is possible to use an apparatus as described above.

The apparatus and the method described above can also be used for a measurement of wave fronts and for an evaluation of phase information contained therein.

The apparatus respectively the method described above may be used together, resp. in combination with, an apparatus respectively a method for a therapeutic (surgical) treatment of the biological tissue, to measure the depth profile of the tissue that is being modified by the treatment and to control the treatment apparatus respectively the treatment method so that a desired depth profile is being generated.

BRIEF DESCRIPTION OF THE DRAWINGS

Embodiments of the invention are described below in more detail with reference to the appended drawings, in which.

DETAILED DESCRIPTION OF THE DRAWINGS

FIG. 1 shows that the degree of transmission respectively the transmissivity of a cornea of the human eye amounts to more than 60% in a range of wavelengths greater than about 325 nm and decreases strongly for shorter wavelengths (by the onset of band absorption). Because of this, the use of wavelength of about 300 nm or less is limited. It has been found that the scattering properties of the cornea in the range of more than 300 nm to 500 nm are particularly favourable, which causes a high signal intensity of the measurement beam deflected (scattered) by the biological tissue.

FIG. 2 illustrates the relationship represented by the equation (1) between the axial resolution $\Delta z$ of an OCT-measurement apparatus, the central wavelength $\lambda_0$ and the spectral width $\Delta\lambda$ of the wavelength spectrum of the light radiation used. It can be seen in FIG. 2, that at a wavelength $\lambda_0$ in the range of 300 to 500 nm a greater axial resolution power (a smaller axial resolution $\Delta z$) is achieved at a comparable spectral bandwidth as compared to wavelength in the range of more than 800 nm, which are being used in present common OCT-measurement apparatuses. FIG. 2 also shows that for wavelengths in the range of 300 to 500 nm, in order to achieve a comparable axial resolution $\Delta z$ as for wavelengths greater than 800 nm, there is required a lower spectral width $\Delta\lambda$ in the wavelength spectrum generated by the light source.

Figure 3:
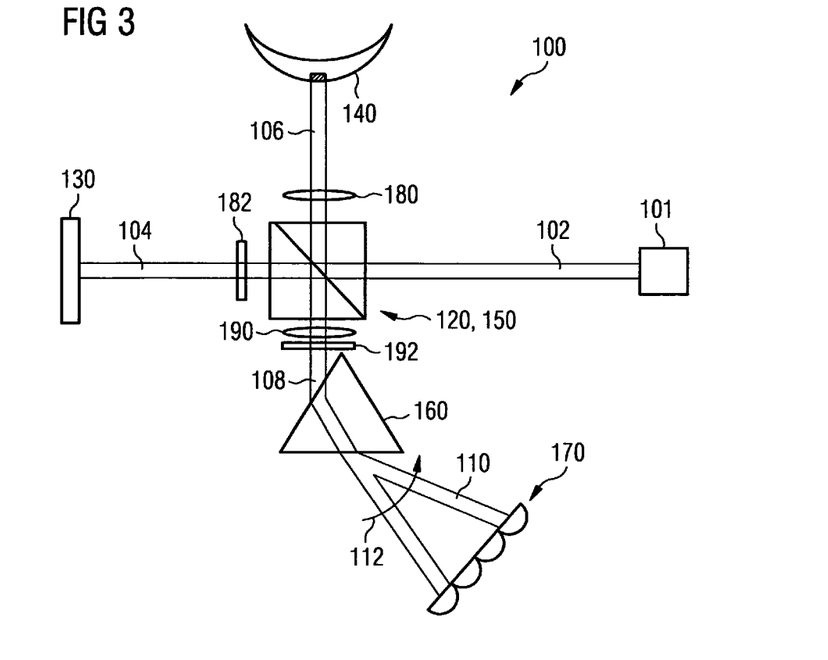
FIG. 3 a principle of a construction of an OCT-measurement apparatus according to the Fourier-domain-OCT principle.

The OCT-measurement apparatus 100 according to the Fourier-domain-OCT principle shown in FIG. 3 comprises a light source 101, which generates a bundle 102 of light beams, a Michelson interferometer arrangement comprising a device 120, 150 for splitting the bundle of light beams into a reference beam 104 and a measurement beam 106 and for superpositioning the reference and measurement beams 104, 106 which are respectively deflected back, into a superpositioned beam 108, a mirror 130 which is spatially fixed, serves as a reference beam deflection device, reflects the reference beam 104 transmitted by the beam splitter device 120 substantially in itself, and directs the measurement beam 106 deflected by the beam splitter device 120 toward the tissue to be investigated, namely a cornea 140 of a human eye, wherein the tissue reflects the measurement beam 106 back into itself. The OCT-measurement apparatus 100 further comprises a spectrometer device 160 configured as a prism, which device 160 spatially separates the superpositioned beam 108 in an angular direction indicated in FIG. 3 by the arrow 112, in dependency from the wavelength, into partial bundles 110 of radiation, and a detector array having a resolution direction which is substantially arranged such that it is capable to receive the partial rays 110 which are deflected selectively, according to the wavelength, and to detect an according spatial distribution of the intensity of the partial bundles 110 of rays.

The tissue to be investigated (the cornea 140) is arranged at a distance with respect to the device 120, 150 such that the optical path length of the measurement beam 106 is approximately equal to the optical path length of the reference beam 104. The depth profile at the point of incidence of the measurement beam 106 on the tissue (the cornea 140) becomes measurable because the wavelength spectrum impinging in the incidence area is separated spatially in a wavelength selective manner in the spectrometer device 160 into the partial rays 110, whereby an intensity maximum is generated by a constructive interference of the measurement beam 106 and the reference beam 104 only for such partial rays out of the totality of all partial rays 110, for which the optical path length difference between the measurement beam 106 and the reference beam 104 just diminishes (becomes zero) or is an integer multiple of the respective wavelength. A position on the detector array 170, where a maximum of the intensity occurs, corresponds to a particular wavelength and thus to a particular optical path length difference between the reference beam 104 and the measurement beam 106, for which the optical path travelled by the measurement light corresponds to the known, fixed optical path of the reference beam, i.e. the penetration depth of which associated with the position of the maximum of the intensity on the detector array 170 within the accuracy the axial resolution power.

In the light path between the device 120, 150 and the tissue to be investigated (the cornea 140) there may also be provided an imaging optical system (not shown). By varying a focal length and/or an axial position of the imaging optical system in the light path between the device 120, 150 and the tissue, the tissue (the cornea 140) is scanned with respect to its depth. By a lateral movement or by a tilting of the imaging optical system, the measurement beam 106 is guided (scanned) laterally across the tissue (the cornea 140) and thus a two-dimensional scanning of the point of incidence of the measurement beam 106 on the tissue resp. a two-dimensional scanning of depth profiles is achieved.

Figure 4:
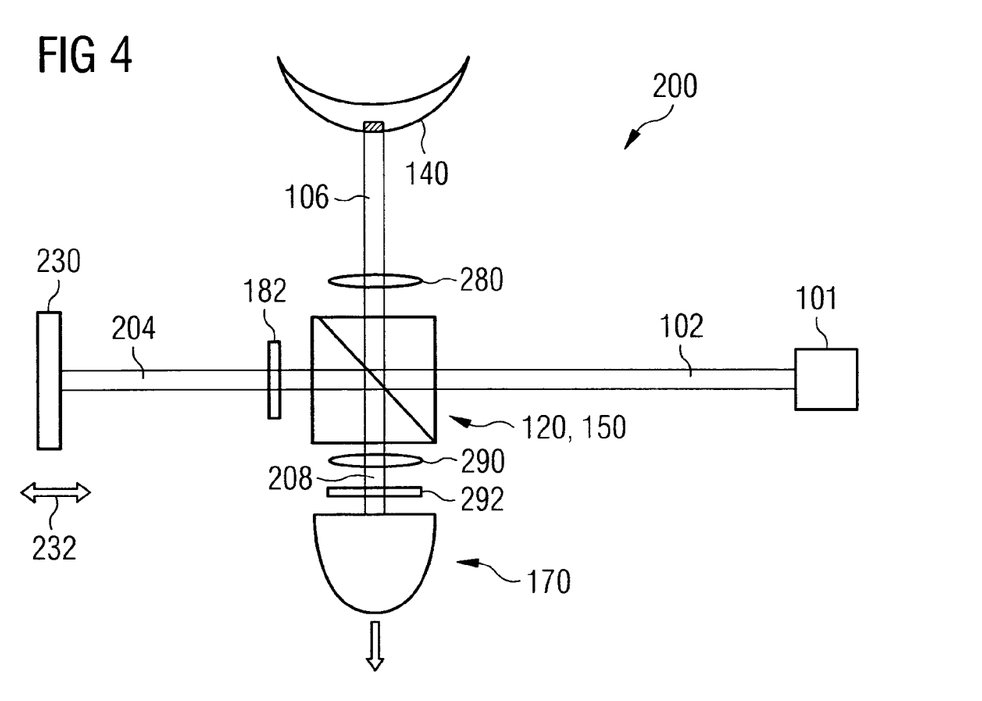
FIG. 4 shows a schematic representation of an OCT-measurement apparatus according to the time-domain-OCT principle.

The OCT-measurement apparatus 200 according to the time-domain-OCT principle shown in FIG. 4 comprises a light source 101 for generating a bundle 102 of light rays, a device 120, 150 for splitting the bundle 102 of light rays into a reference beam 204 and a measurement beam 106, and the tissue to be investigated (the cornea 140), respectively as in the apparatus 100 shown in FIG. 3.

Contrary to the apparatus 100 shown in FIG. 3, the OCT-measurement apparatus 200 comprises a mirror 230 as the reference beam deflection device, which is moved periodically axially (to and fro) in the direction indicated by the arrow 232 shown in FIG. 4, and a spatially fixed detector 270 for receiving the superpositioned beam 208 generated by the device 120, 150 by superpositioning the measurement beam 106 and the reference 204 respectively reflected back, and measuring the intensity thereof (of the superpositioned beam 208) in a temporally resolved manner Due to the movement of the mirror 230, the optical path length travelled by the reference beam 204 is modulated with respect to its length. Each optical path length of the reference beam 204 generated by this modulation corresponds to a particular optical path length travelled by the measurement beam 106, for which the superposition of the reference beam 204 and the measurement beam 106 in the superpositioned beam 208 leads to a constructive interference and thus to a maximum of the intensity (in the course of time). A particular point in time in the measurement of the intensity of the superpositioned beam 208 can therefore be associated to a particular optical path length of the measurement beam 106 and thus a penetration depth of the light reflected back from the tissue (the cornea 140). Similar as for the apparatus 100 shown in FIG. 3, also for the apparatus 200 shown in FIG. 4, there may be provided an optical imaging device (not shown) in the light path between the device 120, 150 and the tissue (the cornea 140), which imaging optical system images (focuses) the measurement beam 106 onto the tissue. By varying the focal length and/or moving the optical imaging device along the direction of the measurement beam 106, the tissue (the cornea 140) is scanned with respect to the penetration depth of the measurement beam 106. By moving the imaging device in a lateral direction with respect to the direction of the measurement beam 106 (optical axis), a two-dimensional scanning across the surface of the tissue (the cornea 140) is achieved.

The OCT-measurement apparatuses 100 and 200 shown, respectively, in the FIGS. 3 and 4 may comprise, for a coherent imaging of the tissue onto the detector 170 and 270, a measurement beam optical system 108 and 208 arranged in the measurement beam 106 and a first reference beam optical system 190 and 290 arranged in the superposition beam 108 and 208. The measurement beam optical system 180 and 280 and the first superposition beam optical system 190 and 290 are advantageous in order to realize the principle of spatially coherently imaging the tissue 140 to be investigated onto the detector 170 and 270.

The OCT-measurement apparatuses 100 and 200 shown, respectively, in the FIGS. 3 and 4 may further comprise in the reference beam 104 and 204 a reference beam optical system 182 and 282 for correcting phase shifts between the reference beam 104 and 204 and the measurement beam 106 and 206 caused by portions of the optical path length of the measurement beam within the tissue 140. The reference beam optical system 182 and 282 may for example be embodied as a liquid display, a plate-shaped LCD system or another device for generating a phase shift, which respectively have advantageously a phase shift that varies in the lateral (x, y) dimension. In a simpler embodiment, the reference beam optical system 182 and 282 may be embodied as a glass plate or an optical element, such as a lens, having a phase shift that is predetermined in dependency of the tissue 140 to be investigated.

And finally, the OCT-measurement apparatuses 100 and 200 shown, respectively, in FIGS. 3 and 4 may further comprise in the superposition beamed 108 and 208 a second superposition beam optical system 192 and 292 for compensating a possible fundamental shape resp. form, in particular for correcting imaging errors caused by a basic shape, for example a basic arching of the biological tissue 140 such as the frontal eye section, arranged in the measurement beam 106 for investigation.

In all the embodiments of the invention described herein above, it is enabled through the use of radiation comprising wavelengths in a wavelength range of more than 300 nm to 500 nm, in comparison to the wavelengths of 800 nm or more which are used in conventional OCT-measurement apparatuses, to use light sources having a lower bandwidth for achieving a comparable resolution power or to achieve a higher resolution power (lower resolution $\Delta z$) with a comparable is bandwidth (respectively in comparison to conventional OCT-measurement apparatuses).

The invention claimed is:

1. Apparatus for recording a depth profile of a biological tissue, including a frontal eye section of a human eye, according to the principle of optical coherence tomography (OCT), comprising:
 a light source that can generate a bundle of light rays having a wavelength spectrum with a predetermined spectral bandwidth ($\Delta\lambda$) and a central wavelength ($\lambda_0$) that is in a predetermined wavelength range from 300 nm to 500 nm;
 an interferometer arrangement comprising:
  a beam splitter device that can spatially separate the bundle of light rays generated by the light source into a reference beam and a measurement beam directed towards the tissue;
  a reference beam deflection device that can deflect the reference beam;
  a beam superpositioning device that can spatially superimpose the deflected reference beam onto the measurement beam deflected by the tissue to a superpositioned beam;
 a detector arrangement that can detect information in the superpositioned beam associated with the difference of the optical path length of the reference beam and the measurement beam.

2. Apparatus according to claim 1, wherein the central wavelength is in a predetermined wavelength range from 350 nm to 450 nm.

3. Apparatus according to claim 1, wherein the light source is a gallium nitride (GaNi)-semiconductor-LED and the predetermined wavelength range is next to 405 nm according to the emission wavelength range of the LED.

4. Apparatus according to claim 1, wherein the interferometer arrangement and the detector arrangement are designed for an operation using wavelengths in the predetermined wavelength range.

5. Apparatus according to claim 1, wherein the apparatus operates according to the principle of the Fourier-domain -OCT.

6. Apparatus according to claim 5, wherein the reference beam runs spatially substantially constant and the detector arrangement comprises:
 a spectrometer device that can separate the superpositioned beam spatially, according to the wavelength, into partial beams having different wavelengths, and
 a spatially resolving detector array that can measure the intensities of the partial rays in a wavelength selective manner.

7. Apparatus according to claim 1, wherein the apparatus operates according to the principle of the time-domain-OCT.

8. Apparatus according to claim 7, wherein:
 the optical path length of the reference beam is modulated temporally,
 the detector arrangement comprises a detector device that can measure the intensity of the superpositioned beam, in which the intensity is temporally modulated by the modulation of the reference beam, in a temporally resolved manner.

9. Apparatus according to claim 1, comprising a measurement beam optical system in the measurement beam and a first superpositioned beam optical system in the superpositioned beam for coherent imaging of the tissue onto the detector arrangement.

10. Apparatus according to claim 1, comprising, in the reference beam, a reference beam optical system for correcting phase shifts between the reference beam and the measurement beam caused by optical path length portions of the measurement beam within the tissue.

11. Apparatus according to claim 1, comprising, in the superpositioned beam, a second superposition beam optical system for correcting imaging errors caused by a predetermined basic shape of the biological tissue, arranged in the measurement beam.

12. Apparatus according to claim 1, wherein the central wavelength is in a predetermined wavelength range from 395 nm to 415 nm.

13. Apparatus according to claim 1, wherein the apparatus operates according to the principle of the parallel Fourier-domain-OCT.

14. Apparatus according to claim 6, wherein the spectrometer device comprises a prism or an optical grating.

15. Apparatus according to claim 1, wherein the apparatus operates according to the principle of the parallel time-domain-OCT.

16. Apparatus according to claim 7, wherein:
the optical path length of the reference beam is modulated temporally by a periodic movement of the reference beam deflection device,
the detector arrangement comprises a detector device that can measure the intensity of the superpositioned beam, in which the intensity is temporally modulated by the modulation of the reference beam, in a temporally resolved manner.

17. Method for measuring a depth profile of a biological tissue, including a frontal eye section of a human eye, according to the principle of optical coherence tomography (OCT), comprising:
generating a bundle of light rays having a wavelength spectrum with a predetermined spectral bandwidth ($\Delta\lambda$) and a central wavelength ($\lambda_0$) that is in a predetermined wavelength range from 300 nm to 500 nm;
spatially separating the bundle of light rays generated by the light source into a reference beam and a measurement beam directed towards the tissue;
deflecting the reference beam;
spatially superimposing the deflected reference beam onto the measurement beam deflected by the tissue to a superpositioned beam;
detecting information in the superpositioned beam associated with the difference of the optical path length of the reference beam and the measurement beam.

18. Method according to claim 17, wherein the central wavelength is in a predetermined wavelength range from 350 nm to 450 nm.

19. Method according to claim 17, wherein the central wavelength is in a predetermined wavelength range from 395 nm to 415 nm.

* * * * *